US006866225B2

(12) United States Patent
Jones et al.

(10) Patent No.: US 6,866,225 B2
(45) Date of Patent: Mar. 15, 2005

(54) METHOD AND SYSTEM FOR PRESENTING MOVING SIMULATED IMAGES IN A MOVING VEHICLE

(75) Inventors: Richard D. Jones, Issaquah, WA (US); Scott C. Pilet, Seattle, WA (US)

(73) Assignee: The Boeing Company, Seattle, WA (US)

( * ) Notice: Subject to any disclaimer, the term of this patent is extended or adjusted under 35 U.S.C. 154(b) by 0 days.

(21) Appl. No.: 10/427,405

(22) Filed: Apr. 30, 2003

(65) Prior Publication Data

US 2004/0217234 A1 Nov. 4, 2004

(51) Int. Cl.[7] .............................................. B64D 11/06
(52) U.S. Cl. ........................ 244/118.5; 701/1; 340/974
(58) Field of Search .......................... 244/118.5, 118.6, 244/122 R; 340/945, 967, 974, 980, 979; 348/148, 117, 118, 145; 701/1, 36

(56) References Cited

U.S. PATENT DOCUMENTS

| | | | | |
|---|---|---|---|---|
| 4,937,751 A | * | 6/1990 | Nimura et al. | 701/211 |
| 5,253,051 A | | 10/1993 | McManigal | |
| 5,610,822 A | * | 3/1997 | Murphy | 701/211 |
| 6,443,913 B1 | * | 9/2002 | Kania | 600/595 |
| 6,497,649 B2 | * | 12/2002 | Parker et al. | 600/27 |
| 6,661,353 B1 | * | 12/2003 | Gopen | 340/973 |
| 6,714,141 B2 | * | 3/2004 | Kennedy | 340/980 |
| 2002/0123829 A1 | * | 9/2002 | Kuriya et al. | 701/1 |
| 2003/0078713 A1 | * | 4/2003 | Tanaka et al. | 701/41 |
| 2003/0083790 A1 | * | 5/2003 | Hattori et al. | 701/1 |
| 2003/0179109 A1 | * | 9/2003 | Chamas et al. | 340/973 |

OTHER PUBLICATIONS http://www.lexus.com/cpo/model_detail/ls/430/2002.html.*
http://www.new-cars.com/2002/lexus/ls430/2002-lexus-ls430-interior.jpg.*
Kaiser, Mary K. et al., "Dynamic Eye-Point Displays," (2 pages) http://vision.arc.nasa.gov/HST/Brief/Vision.S.T./Dynamic.E.html, [Accessed Dec. 4, 2002].

* cited by examiner

Primary Examiner—Peter M. Poon
Assistant Examiner—Timothy D. Collins
(74) Attorney, Agent, or Firm—Perkins Coie LLP (57) ABSTRACT

Methods and systems for presenting images to vehicle occupants are disclosed. A system in accordance with one embodiment of the invention includes at least one display portion configured to display an image and be positioned proximate to a seat location within the vehicle. A first signal receiving portion can be configured to receive an input image signal, and a second signal receiving portion can be configured to receive a motion signal corresponding to a motion of the vehicle. A processing portion can be configured to direct to the at least one display portion a time-varying output signal that appears to move by less than an object actually positioned external to the vehicle would appear to move to an occupant at the seat location of the vehicle. Accordingly, the viewer may be less susceptible to motion sickness by receiving visual cues that correspond to less motion than the occupant feels.

24 Claims, 7 Drawing Sheets

METHOD AND SYSTEM FOR PRESENTING MOVING SIMULATED IMAGES IN A MOVING VEHICLE

CROSS-REFERENCE TO RELATED APPLICATIONS

The present application is related to and incorporates by reference the following U.S. Patent Applications, filed simultaneously herewith:
1. U.S. application Ser. No. 10/427,429 entitled METHOD AND SYSTEM FOR PRESENTING DIFFERENT VIEWS TO PASSENGERS IN A MOVING VEHICLE; and
2. U.S. application Ser. No. 10/427,677 entitled METHOD AND SYSTEM FOR PRESENTING AN IMAGE OF AN EXTERNAL VIEW IN A MOVING VEHICLE.

TECHNICAL FIELD

The present invention relates to methods and systems for presenting moving images in moving vehicles, for example, presenting images simulating objects external to an aircraft to passengers within the aircraft.

BACKGROUND

Some vehicles provide occupants with limited visual access to the region exterior to the vehicle. For example, some trucks and buses provide limited visual access to the region directly behind the vehicle. One method for overcoming this drawback is to provide the vehicle with an aft-pointing camera that is connected to a display panel inside the vehicle. The display panel can accordingly present to the vehicle driver an image of what the driver would see if he or she were able to look through the rear of the vehicle. This system can therefore aid the driver as the driver backs up the vehicle or engages in other maneuvers that benefit from an aft-facing view. Another existing system includes a passenger aircraft seatback display that schematically portrays the aircraft superimposed on a map of the terrain the aircraft overflies. However, the foregoing systems can be limited because they present the same image to one or more viewers. Accordingly, the foregoing systems may not be adequate to provide multiple viewers at different positions within the vehicle with an accurate view of the external world outside the vehicle as the vehicle moves.

SUMMARY

The present invention is directed toward methods and systems for presenting simulated images to occupants of a moving vehicle. A system in accordance with one aspect of the invention includes at least one display portion configured to display an image and be positioned proximate to a seat location within a vehicle. A first signal receiving portion can be configured to receive an input image signal, and a second signal receiving portion can be configured to receive a motion signal corresponding to a motion of the vehicle. A processing portion can be configured to direct to the at least one display portion a time-varying output image signal, with the output image signal corresponding at least in part to the input image signal updated so as to appear to move relative to the at least one display portion by less than an object actually positioned external to the vehicle would appear to move.

In other aspects of the invention, the signal processing portion can be configured to transmit an image signal that forms an image with a first region having a first hue and being positioned above a second region having a second hue, with the first hue lighter than the second hue. The at least one display portion can be elongated generally parallel to a longitudinal axis of the vehicle and can be visually accessible from first and second passenger seats, which are positioned one behind the other along the longitudinal axis. In yet another aspect of the invention, the at least one display portion can include a deployable window shade.

A method in accordance with another aspect of the invention includes directing an image signal to form an image on a display portion, with the display portion being visually accessible to a vehicle occupant, and with the image having a perceived location external to the vehicle. The method can further include receiving a motion signal corresponding to a motion of the vehicle and, based on the motion signal, moving the image relative to the display portion by less than an amount that an object at the perceived location would appear to the occupant to move as the vehicle goes through the motion.

DETAILED DESCRIPTION

The present disclosure describes methods and systems for providing a moving image in a vehicle. The image can be simulated and can appear to viewers to be external to the vehicle. The motion of the image can be controlled, for example, to reduce the viewer's susceptibility to motion sickness. Many specific details of certain embodiments of the invention are set forth in the following description and in FIGS. 1–9 to provide a thorough understanding of these embodiments. One skilled in the art, however, will understand that the present invention may have additional embodiments, and that the invention may be practiced without several of the details described below.

Embodiments of the invention can provide people inside a vehicle with a simulated, time-varying view of an object or objects that appear to be outside the vehicle. In one embodiment, the vehicle can include a passenger aircraft having passenger cabins with few or no passenger windows and the image can be presented on display portions that extend along the walls and/or ceilings of the passenger cabins. For purposes of illustration, aspects of the systems and methods are described in the context of a blended wing body aircraft. In other embodiments, the systems can be incorporated into aircraft having other configurations, and/or vehicles other than aircraft.

Figure 1:
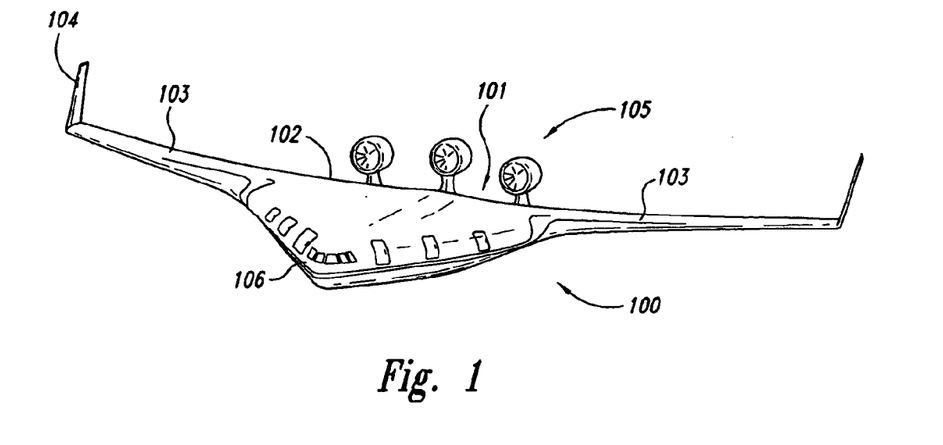
FIG. 1 is a partially schematic, front isometric illustration of an aircraft having a system for directing moving images to viewers within the aircraft in accordance with an embodiment of the invention.
Figure 2:
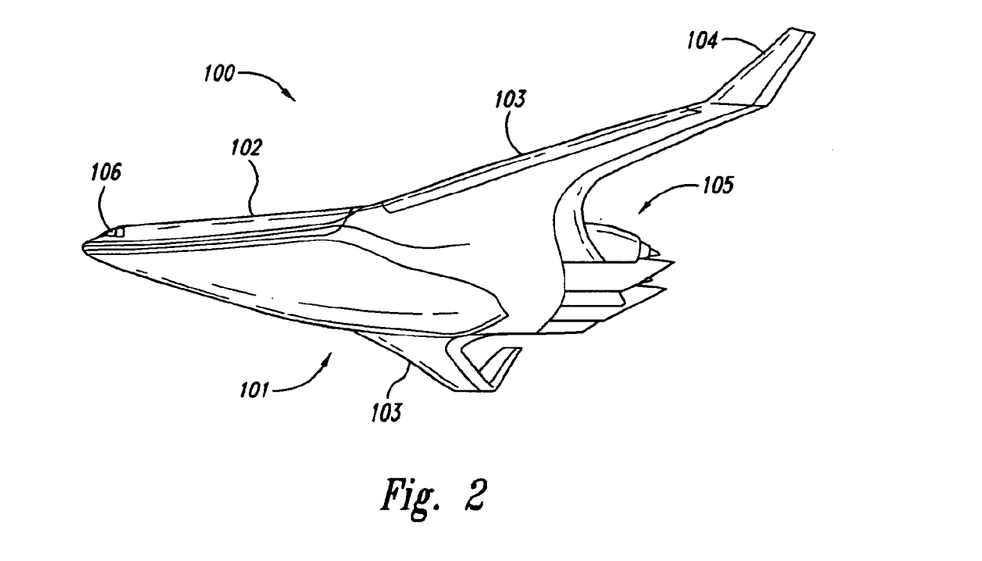
FIG. 2 is a partially schematic bottom isometric view of the aircraft shown in FIG. 1.

FIGS. 1 and 2 are partially schematic illustrations of an aircraft 100 having a blended wing body configuration in accordance with an embodiment of the invention. In one aspect of this embodiment, the aircraft 100 can include a blended wing body 101 having a central portion 102 for carrying a payload. Outboard portions 103 can extend laterally outwardly from the central portion 102. The aircraft 100 can include winglets 104 for lateral stability, and a propulsion system 105 for power. In one aspect of this embodiment, the propulsion system 105 can include three engines mounted above the upper surface of the blended wing body 101, and in other embodiments, the propulsion system 105 can have other arrangements. In any of these embodiments, the central portion 102 can include a forward-facing flight deck 106 from which the aircraft is operated.

Figure 3:
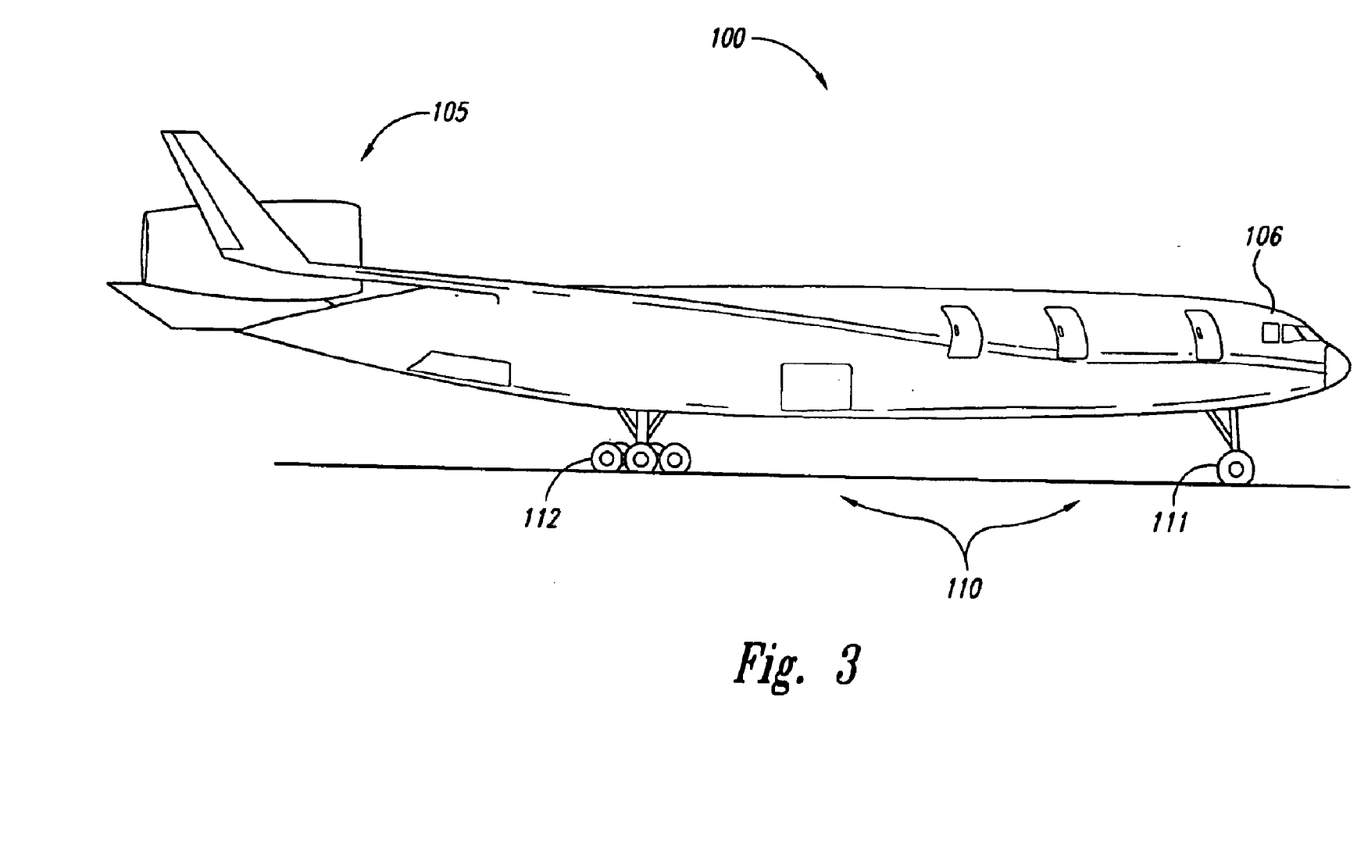
FIG. 3 is a partially schematic, side elevational view of the aircraft shown in FIG. 1.

FIG. 3 is a partially schematic, side elevational view of an embodiment of the aircraft 100 illustrating the blended wing body 101 supported on landing gear 110. The landing gear 110 can include a nose gear 111 and a plurality of main gears 112. In other embodiments, the aircraft 100 can have other landing gear configurations.

Figure 4:
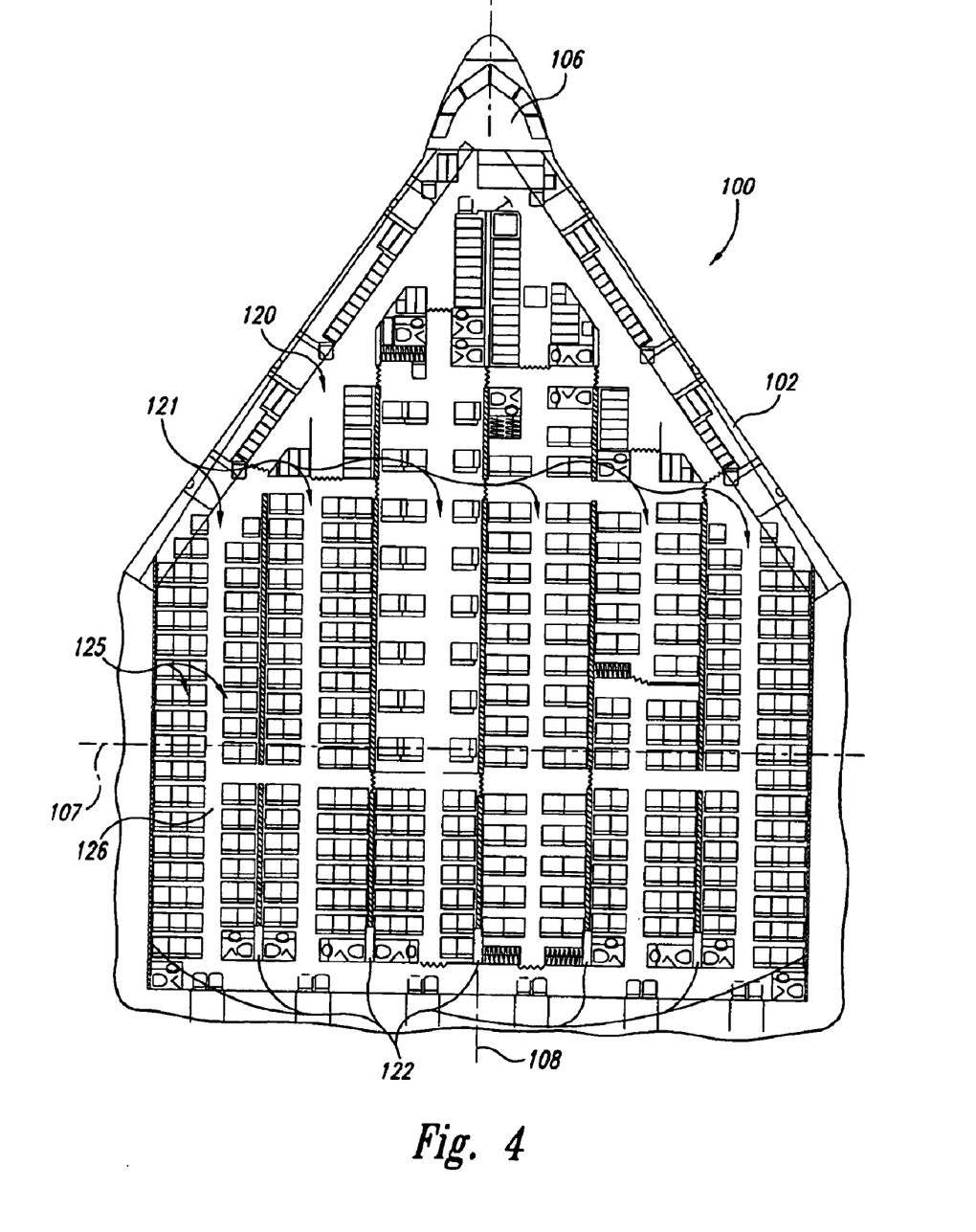
FIG. 4 is a partially schematic, top plan view of an interior of a portion of the aircraft shown in FIGS. 1–3, configured in accordance with an embodiment of the invention.

FIG. 4 is a partially schematic, top plan view of an interior portion of the aircraft 100, configured in accordance with an embodiment of the invention. In one aspect of this embodiment, the interior portion includes a passenger compartment 120 positioned aft of the flight deck 106. The passenger compartment 120 can be divided into a plurality of passenger bays 121 separated from each other by partitions 122. In a further aspect of this embodiment, each passenger bay 121 can be elongated in a direction generally parallel to a longitudinal or roll axis 108 of the aircraft 100 and generally perpendicular to a pitch axis 107 of the aircraft. Each passenger bay 121 can house passenger seats 125 separated by aisles 126 which are also aligned generally parallel to the longitudinal axis 108. In other embodiments, the interior of the aircraft 100 can have other passenger seating arrangements.

In any of the embodiments described above with reference to FIGS. 1–4, one characteristic of the aircraft 100 is that at least some of the seats 125 are not adjacent to a window and therefore passengers (not shown) in those seats do not have direct visual access to the region exterior to the aircraft 100. In fact, in at least one embodiment, the aircraft 100 can include few or no windows other than those at the flight deck 106. An advantage of a windowless (or reduced window) passenger compartment 120 is that it can allow for the efficient use of a relatively wide interior space, for example, the space provided by a blended wing body design. A further advantage is that eliminating or reducing the number of windows in the passenger compartment 120 can reduce the cost of manufacturing and/or maintaining the aircraft 100. However, the lack of windows may be uncomfortable for some passengers and may increase the likelihood that some passengers suffer from air sickness because they do not have access to visual cues that correspond in some manner with the motion they feel. Accordingly, an embodiment of the invention described below with reference to FIGS. 5–9 includes a system and method for presenting to the passengers a series of images that simulate or represent the view external to the aircraft, in a manner that corresponds, at least in part, with the motion the passenger feels.

Figure 5:
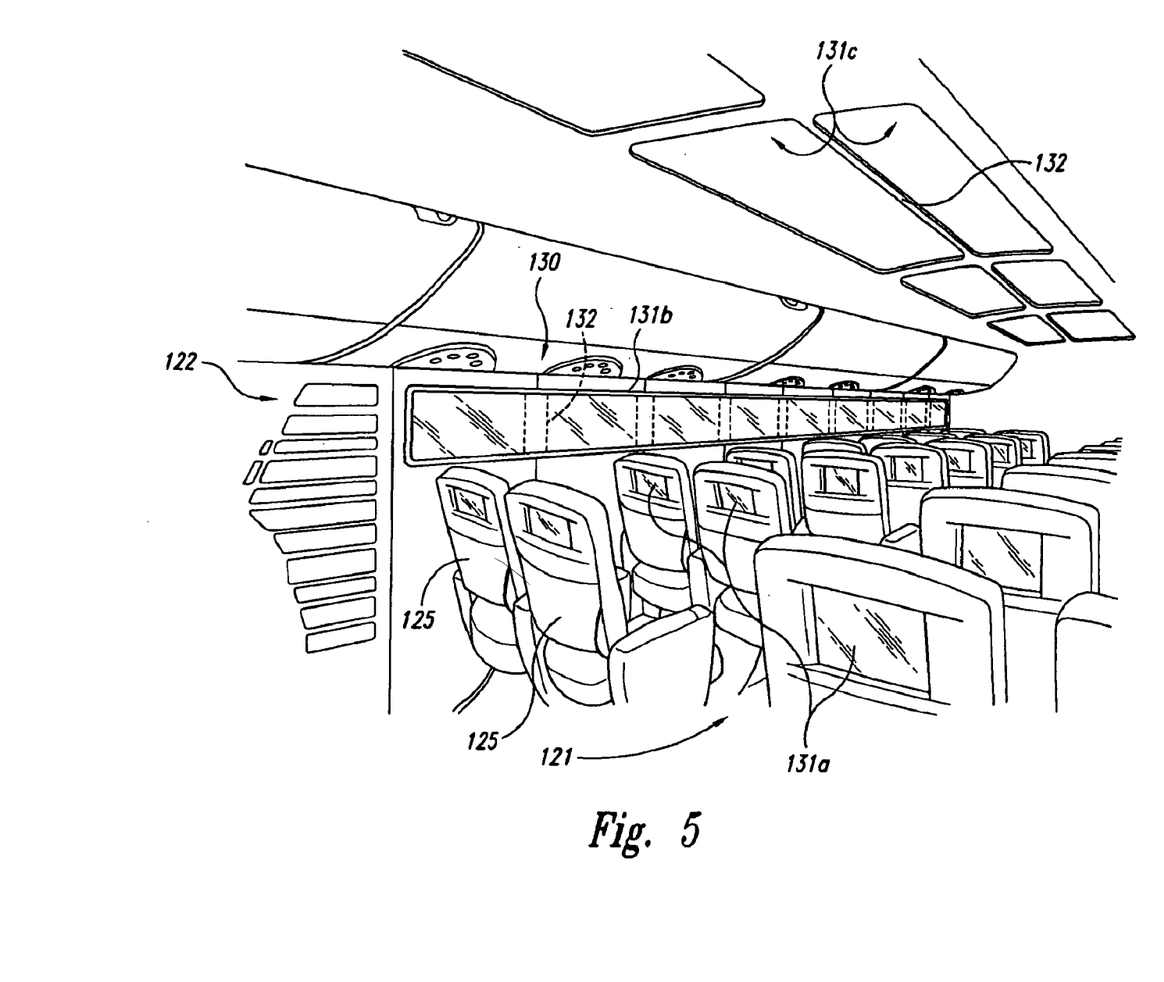
FIG. 5 is a partially schematic, forward-looking isometric illustration of the interior of a portion of an aircraft configured in accordance with an embodiment of the invention.

FIG. 5 is a partially schematic, forward looking view of a passenger bay 121 configured in accordance with an embodiment of the invention. In one aspect of this embodiment, the passenger bay 121 includes a display 130 having one or more portions that present to the passengers images that move in a manner that is at least partially coupled to the movement of the aircraft. For example, the display 130 can include a plurality of display portions 131, shown in FIG. 5 as forward display portions 131a positioned in the backs of the seats 125, side display portions 131b positioned laterally adjacent to the seats 125, and/or top display portions 131c located above the seats 125. The display portions 131 can be formed from a variety of suitable components, including liquid crystal display panels and/or matrices of light emitting diodes, both of which are commercially available. One source for suitable display panels is Universal Display Corp. of Ewing, N.J. In one embodiment, the side display portions 131b and the top display portions 131c can include separators 132, and the same image can be duplicated in each of the cells partitioned by the separators 132. In another embodiment, the separators 132 can be eliminated. In a further aspect of these embodiments, a continuous image (that spans across the separators 132, if the separators 132 are present) can be provided on each display portion 131 and can present to the passengers movies, games, newscasts, safety demonstrations and/or other materials selected by the passengers and/or the crew. In another embodiment, the image presented on each forward display portion 131a can be a duplicate of the image presented on the neighboring forward display portion, and this arrangement can be applied to the side display portions 131b and/or the top display portions 131c. In any of the foregoing embodiments, the display portions 131 can also present simulated images that move in a manner that is at least partially coupled to the movement of the aircraft, as described in greater detail below.

Figure 6A:
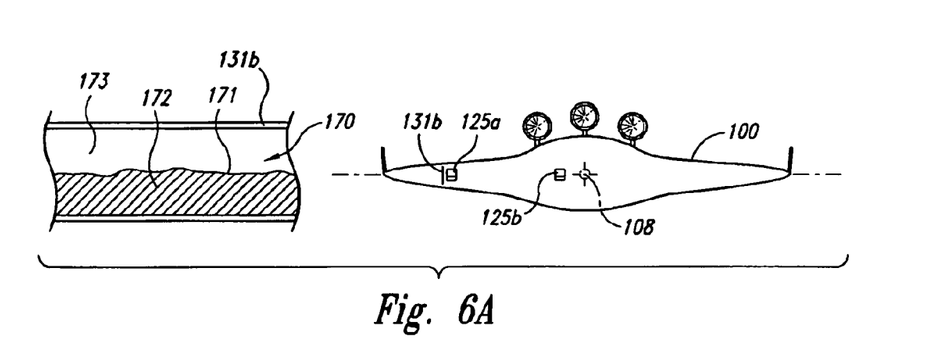
FIGS. 6A–6C illustrate a maneuvering aircraft and corresponding images displayed within the aircraft in accordance with an embodiment of the invention.
Figure 6B:
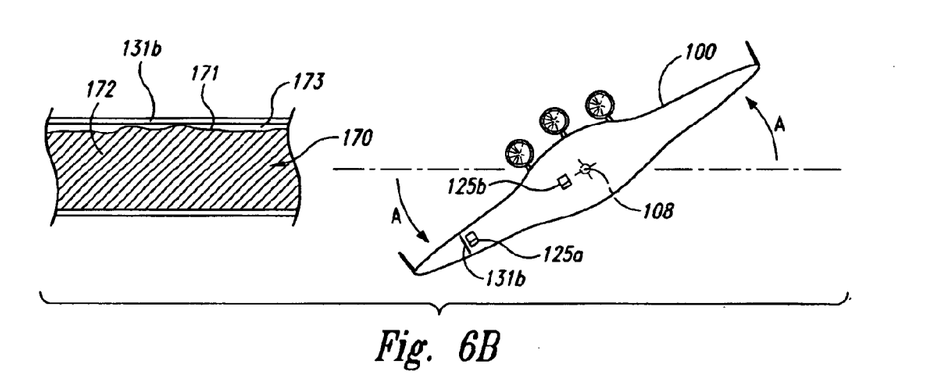
Figure 6C:
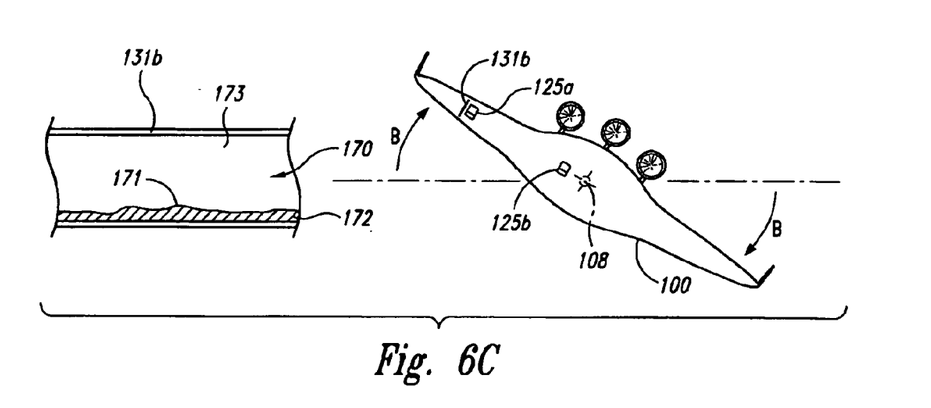

FIGS. 6A–6C illustrate a partially schematic rear view of the aircraft 100 (and part of a corresponding side display portion 131b located within the aircraft 100) as the aircraft 100 rolls about its roll axis 108. Beginning with FIG. 6A, the aircraft 100 can include an outboard seat 125a positioned adjacent to or proximate to the side display portion 131b, and an inboard seat 125b positioned inboard of the outboard seat 125a. Accordingly, the inboard seat 125b is closer to the roll axis 108 than is the outboard seat 125a. When the aircraft 100 is in a neutral position relative to the roll axis 108 (as shown in FIG. 6A), the side display portion 131b can present an image 170, also shown schematically in FIG. 6A. In one aspect of this embodiment, the image 170 can include a horizon 171, a light region 173 above the horizon 171, and a dark region 172 below the horizon 171. The image 170 can be entirely simulated. For example, the horizon 171 can have a contour that is not necessarily representative of the actual horizon outside the aircraft 100, and the light region 173 and the dark region 172 can be presented even if the aircraft 100 is flying at night. In still further embodiments, the image 170 can have features other than the horizon 171, light region 173 and dark region 172, that move relative to the side display portion 131b in a manner generally similar to that described below with reference to FIGS. 6B–6C.

Referring now to FIG. 6B, the aircraft 100 is shown after having rolled to the left through an angle A. The image 170 has been updated so that the horizon 171 moves upward relative to the edges of the side display portion 131b. Accordingly, the area occupied by the light region 173 is reduced compared to that shown in FIG. 6A, and the region occupied by the dark region 172 is increased compared to that shown in FIG. 6A.

In a further aspect of this embodiment, the amount by which the horizon 171 moves as the aircraft 100 rolls through angle A can be less than the actual horizon would appear to move to a passenger seated in the outboard seat 125a, if the passenger could see through the fuselage of the aircraft 100. For example, if the side display portion 131b were a window through which a passenger seated in the outboard seat 125a could view the region external to the aircraft 100, the passenger would not see a horizon at all, but would instead see only the ground beneath the aircraft. However, the image 170 provided on the side display portion 131b (which does include the horizon 171) is more representative of what a passenger seated closer to the roll axis 108 (such as a passenger seated at the inboard seat 125b) would see if that passenger could see through the fuselage of the aircraft 100. An advantage of this arrangement is that the passenger seated at the outboard seat 125a may be less susceptible to motion sickness because the horizon 171 appears to that passenger to move by less than would the actual horizon external to the aircraft 100. Put another way, in one embodiment, passengers who normally might experience motion sickness when the aircraft undergoes major movements may not experience motion sickness when they receive visual cues that correspond to a minor movement of the aircraft, even as the aircraft undergoes the major movements.

FIG. 6C illustrates an embodiment of the image 170 presented at the side display portion 131b as the aircraft 100 rolls right through an angle B. The horizon 171 shown in FIG. 6B may appear to move to the passenger seated in the outboard seat 125a by less than would the actual horizon if the passenger could see through the fuselage of the aircraft 100, in a manner generally similar to that described above. Accordingly, and as described above, the passenger may be less susceptible to motion sickness.

In other embodiments, the foregoing method can be applied to displays presenting images that correspond to motion about other axes of the aircraft. For example, the forward display portions 131a can present images that move in a manner generally similar to that described above with reference to FIGS. 6A–6C as the aircraft pitches up and down about the pitch axis 107 (FIG. 4). That is, passengers seated far away from the pitch axis 107 may be presented with an image that moves in a manner generally similar to an object outside the aircraft, as perceived by a passenger at or close to the pitch axis 107.

In still further embodiments, the image presented to the passengers in the aircraft 100 can have other arrangements. For example, the image need not include a horizon 171, a light region 173 or a dark region 172, so long as the features move in a manner that is coupled at least in part to the motion of the aircraft 100, and, in a particular embodiment, appear to move by less than would an actual object outside the aircraft.

Figure 7:
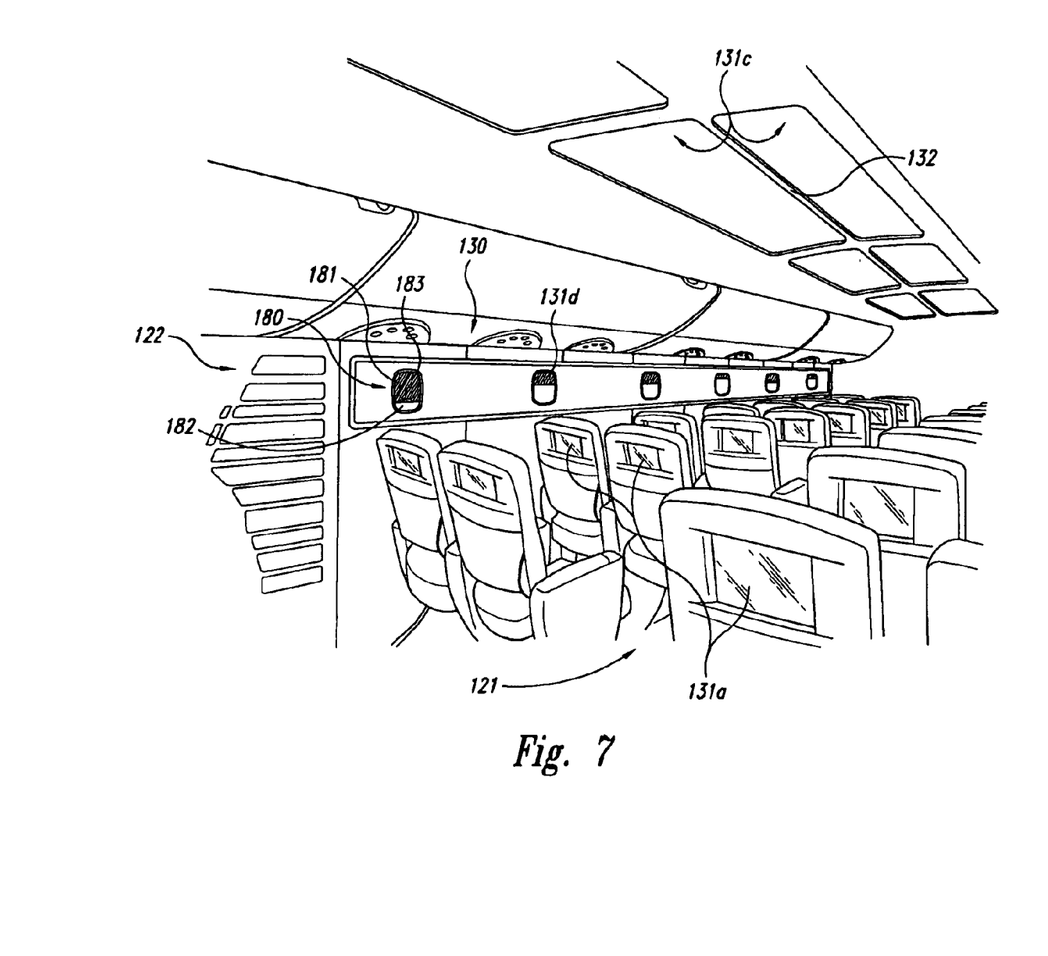
FIG. 7 is a partially schematic, forward looking isometric illustration of an interior of a portion of an aircraft configured in accordance with an embodiment of the invention.

FIG. 7 is a partially schematic view of a passenger bay 121 configured in accordance with another embodiment of the invention. In one aspect of this embodiment, the passenger bay 121 can include a plurality of windows 180 in addition to or in lieu of the side display portion 131b. Each window 180 can include a frame 181 surrounding one or more panes 182. A shade 183 can be movably positioned over the pane or panes 182 and can be moved between a stowed position and a deployed position. In a further aspect of this embodiment, the shade 183 can include a shade-mounted display portion 131d. The display portion 131d can include a liquid crystal display panel, a matrix of LEDs or other suitable display media. Accordingly, the display portion 131d can present a simulated image to a passenger having visual access to the deployed shade 183. The simulated image can include features that move in a manner generally similar to that described above with reference to FIGS. 6A–6C. An advantage of this arrangement is that if the passenger finds that viewing a simulated object (for example, a simulated object that moves by less than an actual object outside the aircraft) reduces the passenger's susceptibility to motion sickness, the passenger can pull down the shade 183 to view the display portion 131d rather than the scene outside the aircraft 100. Another advantage is that the display portion 131d can present to the passenger visual cues during times when such visual cues are not normally available. For example, when the aircraft 100 flies at night, the passenger can pull down the shade 183 to receive visual cues that can reduce the passenger's susceptibility to motion sickness as the aircraft undergoes the maneuvers.

Figure 8:
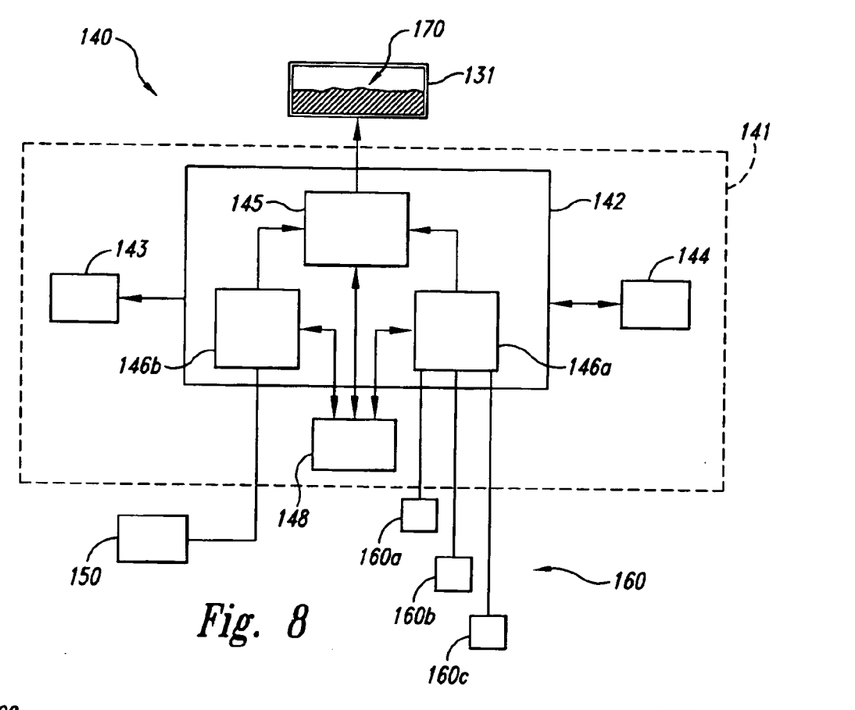
FIG. 8 is a partially schematic block diagram of a system for providing moving images to vehicle occupants in accordance with an embodiment of the invention.

FIG. 8 is a schematic illustration of a system 140 configured to provide passengers with a simulated image that is at least partially coupled to the motion of the aircraft 100 or other vehicle the passenger occupies. The system 140 can include an image source 150 that provides the data for the simulated image, and a plurality of motion sensors 160. A computer 141 can receive signals provided by the image source 150 and the motion sensors 160. In one embodiment, the image source 150 can be external to the computer 141 and in another embodiment, the image source 150 can be integrated with the computer 141. For example, the image source 150 can include a portion of a computer memory 148, which can also store other relevant data. In either embodiment, the computer 141 can manipulate the image data received from the image source 150, based upon the signals received from the motion sensors 160 to provide images that move in a manner generally similar to that described above. The motion sensors 160 can include a roll axis sensor 160a (for detecting rolling motion about the roll axis 108), a pitch axis sensor 160b (for detecting pitch motion about the pitch axis 107) and/or a yaw axis sensor 160c for detecting motion about a yaw axis of the aircraft 100. These sensors 160a–160c can be integrated into a single device, such as an inertial sensor system. Each sensor 160 can provide position, velocity and/or acceleration information for rotational motion relative to the respective axis.

The computer 141 can include a system I/O portion 144 (such as a keyboard) to allow inputs to the system 140, and a diagnostic system display 143 to provide status signals corresponding to the operation of the system 140. The computer 141 can further include a processor 142 having a first signal receiving portion 146a that receives first input signals from the motion sensors 160. A second signal receiving portion 146b can receive second input signals from the image source 150. A signal processing portion 145 can receive the input signals from the signal receiving portions 146a, 146b and can direct an output image signal to the display 131 to provide the image 170. In a particular aspect of this embodiment, the signal processing portion 145 is configured to update the output image signal based at least in part on the signals received from the motion sensors 160 to move the image 170 relative to the display portion 131b by less than an object actually positioned external to the vehicle would appear to move to an occupant proximate to the display portion 131.

In a particular embodiment, the processing portion 145 can receive a digital representation of an image from the image source, and can receive a digital representation of the motion of the aircraft 100 from one or more of the motion sensors 160. Rather than updating the incoming image to correspond to the entire extent of the motion identified by the motions sensors 160, the processing portion 145 can update the image (and transmit a corresponding output signal) to present a view the passenger would see if the aircraft 100 underwent less than the actual motion. As the aircraft returns to a neutral position (for example, zero degrees of rotation about the roll axis), the processing portion 145 can transmit output signals corresponding to images that return to the view as it would appear from the neutral position. In one embodiment, this operation can be performed for motion about the roll axis 108 and can be displayed on the side display portions 131b (FIG. 5). In other embodiments, the operation can be performed for motion about other axes and can be displayed on other display portions 131. For example, the operation can be performed for motion about the pitch axis 107 and displayed on the forward display portions 131a. In one embodiment, the degree to which the motion of the image presented to the passenger is reduced (compared to what the passenger would actually see through a window) is directly proportional to the distance between the passenger (or the display portion) and the rotation axis. Accordingly, the system 140 can perform different calculations for different display portions positioned at different distances from the rotation axis. In one aspect of this embodiment, the system 140 can include a list or register (for example in the memory 148) of the location of each display portion relative to the relevant rotation axis. The system 140 can receive information from the register to determine how much to reduce the motion of the corresponding image. In other embodiments, the motion reduction can be computed in other manners.

Figure 9:
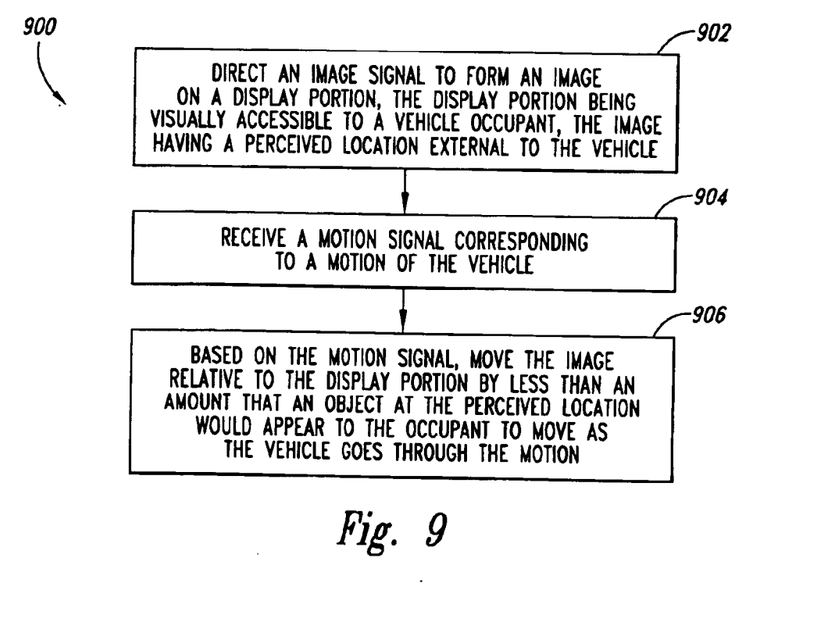
FIG. 9 is a block diagram illustrating a method for presenting a moving image in accordance with an embodiment of the invention.

FIG. 9 is a flow diagram illustrating a process 900 in accordance with an embodiment of the invention. The process 900 can include directing an image signal to form an image on a display portion, with the display portion being visually accessible to a vehicle occupant, and with the image having a perceived location external to the vehicle (process portion 902). In process portion 904, the process 900 includes receiving a motion signal corresponding to the motion of the vehicle. In process portion 906, the image is moved relative to the display portion (based on the motion signal) by less than an amount that an object at the perceived location would appear to the occupant to move, as the vehicle goes through the motion. As described above, this arrangement can reduce the likelihood for the occupant to suffer from motion sickness.

One feature of systems and methods described above with reference to FIGS. 1–9 is that the image presented to occupants of a vehicle (such as an aircraft) can appear to move by less than would the actual scene that the occupant would see if the occupant could see through the walls of the vehicle. An advantage of this feature is that this image may reduce the occupant's susceptibility to motion sickness.

Another feature of an embodiment of the systems and methods described above with reference to FIGS. 1–9 is that images, such as the images described above, can be presented on a display portion that is elongated generally parallel to a longitudinal axis of the vehicle. Different parts of the image presented on the display portion can be visually accessible to passengers positioned at different locations along the longitudinal axis. Accordingly, an advantage of this arrangement is that the same image can be presented to different passengers aligned along an axis, each of which can see a different portion of a unified consistent view.

Still another aspect of embodiments of the systems and methods described above is that the display portions can be deployable. For example, the display portions can be positioned on window shades or simulated window shades. An advantage of this arrangement is that the passengers or other vehicle occupants can determine when they would like to view an image (such as the simulated moving image described above) or, if available, an actual view of the scene exterior to the vehicle.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

What is claimed is:

1. A system for providing an image to a vehicle occupant, comprising:
    at least one display portion configured to display an image and be positioned proximate to a seat location within a vehicle;
    a first signal receiving portion configured to receive an input image signal;
    a second signal receiving portion configured to receive a motion signal corresponding to a motion of the vehicle; and
    a processing portion coupled among the signal receiving portions and the at least one display portion, the processing portion being configured to direct to the at least one display portion a time-varying output image signal, the output image signal corresponding at least in part to the input image signal updated so as to appear to an occupant at the seat location of the vehicle to move in a manner corresponding to a motion that is less than the vehicle motion.

2. The system of claim 1 wherein the first signal receiving portion is configured to receive an input image signal corresponding to an image having a perceived location external to the vehicle.

3. The system of claim 1 wherein the vehicle includes an aircraft configured to roll during flight about a roll axis, and wherein the signal receiving portion is configured to receive a motion signal corresponding to a rolling motion of the aircraft.

4. The system of claim 1 wherein the processing portion is configured to direct an output image signal that includes a representation of a horizon.

5. The system of claim 1 wherein the signal processing portion is configured to direct an image signal that forms an image having a first region with a first hue positioned above a second region having a second hue, wherein the first hue is lighter than the second hue.

6. The system of claim 1, further comprising a motion sensor positioned to detect the motion of the vehicle, the motion sensor being operatively coupled to the first signal receiving portion to direct the motion signal to the signal receiving portion.

7. The system of claim 1 wherein the processing portion includes a computer processor.

8. The system of claim 1 wherein the at least one display portion is moveable between a first position and a second position, with the at least one display portion being deployed and visually accessible to a passenger when in the first position.

9. The system of claim 1 wherein the at least one display portion includes a deployable window shade.

10. The system of claim 1 wherein the vehicle includes an aircraft having a plurality of seats, including a first seat and a second seat positioned aft of the first seat, and wherein the at least one display portion is configured to be visually accessible to occupants in both the first and second seats.

11. The system of claim 1 wherein the vehicle includes an aircraft having a plurality of seats, including a first seat and a second seat positioned aft of the first seat, and wherein the at least one display portion is configured to be visually accessible to occupants in both the first and second seats, further wherein the processing portion is configured to transmit an image that is generally continuous across the first and second display portions.

12. The system of claim 1 wherein the at least one display portion includes a liquid crystal display.

13. The system of claim 1 wherein the at least one display portion includes a matrix of light emitting diodes.

14. A system for processing images corresponding to a view external to a vehicle, comprising:

display means for displaying an image, the display means being visually accessible to a vehicle occupant;

first receiving means for receiving an input image signal;

second receiving means for receiving a motion signal corresponding to a motion of the vehicle; and processing means for directing to the display means a time-varying output signal updated at least in part so as to appear to the vehicle occupant to move in a manner corresponding to a motion that is less than the vehicle motion.

15. The system of claim 14 wherein the vehicle includes an aircraft configured to roll during flight about a roll axis, and wherein the second receiving means are configured to receive a motion signal corresponding to a rolling motion of the aircraft.

16. The system of claim 14 wherein the processing means are configured to direct an image signal that forms an image, the image including a representation of a horizon.

17. The system of claim 14 wherein the display means are moveable between a first position and a second position, with the display means being deployed and visually accessible to the vehicle occupant when in the first position.

18. The system of claim 14 wherein the display means include a deployable window shade movable between a stowed position and a deployed position, with the display means being visually accessible to a vehicle occupant when in the deployed position.

19. A method for providing an image to a vehicle occupant, comprising:

directing an image signal to form an image on a display portion, the display portion being visually accessible to a vehicle occupant, the image having a perceived location external to the vehicle;

receiving a motion signal corresponding to a motion of the vehicle; and based on the motion signal, moving the image relative to the display portion in a manner corresponding to a motion that is less than the motion of the vehicle.

20. The method of claim 19 wherein the vehicle includes an aircraft configured to roll during flight about a roll axis, and wherein receiving a motion signal includes receiving a motion signal corresponding to a rolling motion of the aircraft.

21. The method of claim 19 wherein directing an image signal includes directing an image signal that includes a representation of a horizon.

22. The method of claim 19 wherein directing an image signal includes directing an image signal that forms an image with a first region having a first hue positioned above a second region having a second hue, wherein the first hue is lighter than the second hue.

23. The method of claim 19, further comprising moving the display portion between a first position and a second position, with the display portion being deployed and visually accessible to a passenger when in the first position.

24. The method of claim 19 wherein the display portion includes a deployable window shade, and wherein the method further comprises moving the window shade from a stowed position to a deployed position, with the display portion being visually accessible to a passenger when in the deployed position.

* * * * *